US010582992B2

(12) United States Patent
Jaisson

(10) Patent No.: US 10,582,992 B2
(45) Date of Patent: Mar. 10, 2020

(54) METHOD FOR DETERMINING A MAPPING OF THE CONTACTS AND/OR DISTANCES BETWEEN THE MAXILLARY AND MANDIBULAR ARCHES OF A PATIENT

(71) Applicant: MODJAW, Ste Helene du Lac (FR)

(72) Inventor: Maxime Jaisson, Les Marches (FR)

(73) Assignee: MODJAW, Ste Helene du Lac (FR)

(\*) Notice: Subject to any disclaimer, the term of this patent is extended or adjusted under 35 U.S.C. 154(b) by 22 days.

(21) Appl. No.: 15/560,707

(22) PCT Filed: Mar. 25, 2016

(86) PCT No.: PCT/FR2016/050676
§ 371 (c)(1),
(2) Date: Sep. 22, 2017

(87) PCT Pub. No.: WO2016/151263
PCT Pub. Date: Sep. 29, 2016

(65) Prior Publication Data
US 2018/0104036 A1    Apr. 19, 2018

(30) Foreign Application Priority Data
Mar. 25, 2015   (FR) ...................................... 15 52508

(51) Int. Cl.
*A61C 19/05*       (2006.01)
*G06T 17/20*       (2006.01)
(52) U.S. Cl.
CPC .............. *A61C 19/05* (2013.01); *G06T 17/20* (2013.01); *G06T 2210/41* (2013.01)
(58) Field of Classification Search
None
See application file for complete search history.

(56) References Cited

U.S. PATENT DOCUMENTS

| 5,873,721 A | 2/1999 | Willoughby |
| 6,334,853 B1 | 1/2002 | Kopelman et al. |

(Continued)

FOREIGN PATENT DOCUMENTS

| JP | 002010017467 | 1/2010 |
| JP | 002013240534 | 12/2013 |
| WO | WO-2013030511 | 3/2013 |

OTHER PUBLICATIONS

FR Preliminary Search Report dated Jan. 15, 2016, FR Application No. 1552508 with English translation cover sheet.
(Continued)

*Primary Examiner* — Yanna Wu
(74) *Attorney, Agent, or Firm* — Womble Bond Dickinson (US) LLP

(57) ABSTRACT

The invention relates to a method for determining a mapping of the contacts and/or distances between the teeth of the maxillary arch and the mandibular arch of a patient, characterised in that it comprises the following steps:
 obtaining the mandibular kinematics recorded on the patient;
 obtaining surface meshes of the maxillary arch and the mandibular arch and registering said meshes relative to one another;
 creating a reduced mesh of at least one of said arches, comprising the selection, in the mesh of said arch, of the cells in which the nodes are located at a distance of less than 1 cm from the mesh of the opposite arch;
 creating, for each cell of said reduced mesh, a bounding box comprising a plurality of voxels surrounding said cell;
 using the mandibular kinematics, calculating a network of contacts comprising, for each voxel of the bounding box, information on the existence of a contact between said voxel and a node of the mesh of the opposite arch
(Continued)

during a relative movement of the mandibular arch in relation to the maxillary arch.

10 Claims, 3 Drawing Sheets

(56) References Cited

U.S. PATENT DOCUMENTS

| | | | |
|---|---|---|---|
| 6,621,491 B1* | 9/2003 | Baumrind | A61C 7/08 345/419 |
| 8,013,853 B1 | 9/2011 | Douglas et al. | |
| 2003/0214501 A1 | 11/2003 | Hultgren et al. | |
| 2004/0220691 A1 | 11/2004 | Hofmeister et al. | |
| 2005/0089213 A1 | 4/2005 | Geng | |
| 2009/0316966 A1* | 12/2009 | Marshall | A61B 6/5217 382/128 |
| 2011/0254839 A1 | 10/2011 | Hammer | |
| 2012/0072177 A1 | 3/2012 | Manai et al. | |
| 2013/0120358 A1* | 5/2013 | Fan | G06T 13/00 345/419 |
| 2013/0317800 A1* | 11/2013 | Wu | A61C 13/0004 703/11 |
| 2014/0186793 A1* | 7/2014 | Kurti, Jr. | A61B 5/742 433/73 |
| 2014/0294273 A1 | 10/2014 | Jaisson | |

OTHER PUBLICATIONS

International Search Report dated Jun. 27, 2016, PCT Application No. PCT/FR2016/050676.

* cited by examiner

METHOD FOR DETERMINING A MAPPING OF THE CONTACTS AND/OR DISTANCES BETWEEN THE MAXILLARY AND MANDIBULAR ARCHES OF A PATIENT

FIELD OF THE INVENTION

The present invention relates to a method for determining a mapping of the contacts and/or distances between the teeth of the maxillary arch and the mandibular arch of a patient.

BACKGROUND OF THE INVENTION

The recording of the mandibular kinetics of a patient has enabled considerable progress in the design of dental appliances. Indeed, this recording makes it possible to animate three-dimensional models of dental arches and to visualise in particular the relationship between the teeth. This digital simulation makes it possible to dispense with the mechanical articulators used traditionally.

The document WO 2013/030511 describes a method for designing a dental apparatus which implements a recording of the mandibular kinetics of the patient.

This method firstly comprises either obtaining a volumetric image of the facial skeleton by a tomodensitometric technique, or determining reference planes of the facial skeleton by locating points of interest on the face of the patient.

Furthermore, three-dimensional models of the dental arches of the patient are obtained. Said models, positioned with respect to each other during their creation, are registered with the volumetric image of the facial skeleton or the reference planes determined beforehand.

The recording of the mandibular kinetics is implemented by equipping the patient with a marker attached to the forehead of the patient and markers attached directly to the teeth of the mandibular arch or to the mandible through a support, and by locating and recording the displacements of said markers by means of a camera during mandibular movements of the patient.

The mandibular kinetics thereby recorded may be applied to three-dimensional models of the arches to obtain a digital simulation of the relative displacement of the two arches.

A criterion of interest for the practitioner tasked with designing a dental apparatus is the configuration of interdental contacts.

It would thus be desirable to be able to exploit the mandibular kinetics recorded to obtain a mapping of the interdental contacts or distances between the teeth of the two arches.

However, the determination of these mappings requires a considerable computing time on account of the size of the digital models to handle.

BRIEF DESCRIPTION OF THE INVENTION

One aim of the present invention is to establish a mapping of the contacts and/or distances between the teeth of the two arches in a limited computing time.

According to the invention, a method is proposed for determining a mapping of the contacts and/or distances between the teeth of the maxillary arch and the mandibular arch of a patient, characterised in that it comprises the following steps:
  obtaining the mandibular kinetics recorded on the patient, said mandibular kinetics being recorded by locating and recording, by means of a camera, the displacements of markers attached on the one hand to the forehead of the patient and on the other hand to the mandibular arch, during mandibular movements of the patient,
  obtaining surface meshes of the maxillary arch and the mandibular arch and registering said meshes relative to one another,
  creating a reduced mesh of at least one of said arches, comprising the selection, in the mesh of said arch, of the cells in which the nodes are located at a distance of less than 1 cm from the mesh of the opposite arch,
  creating, for each cell of said reduced mesh, a bounding box comprising a plurality of voxels surrounding said cell,
  using the mandibular kinetics, calculating a network of contacts comprising, for each voxel of the bounding box, information on the existence of a contact between said voxel and a node of the mesh of the opposite arch during a relative movement of the mandibular arch in relation to the maxillary arch.

According to one embodiment of the invention, the method further comprises:
  for each node of said reduced mesh, determining, using the network of contacts, the existence or not of a contact between said node and a node of the mesh of the opposite arch,
  applying a colour representative of the existence of a contact to each cell comprising a node for which a contact has been detected, and
  displaying said colour on each respective cell of the mesh of the arch, so as to form a map of the contacts between the teeth of the two arches.

According to one embodiment, the mandibular kinetics is applied to animate the meshes of the arches and in that the display of colour during this animation is updated.

According to one embodiment, during the updating of the display, the prior display is conserved temporarily and it is progressively attenuated.

According to one embodiment of the invention, the method further comprises:
  for each node of said reduced mesh, determining, using the network of contacts, the distance between said node and a node of the mesh of the opposite arch,
  applying a colour representative of said distance to each cell comprising said node, and
  displaying said colour on each respective cell of the mesh of the arch, so as to form a map of the distances between the teeth of the two arches.

According to one embodiment, the mandibular kinetics is applied to animate the meshes of the arches and the display of colour during this animation is updated.

In a particularly advantageous manner, the reduced mesh is partitioned in the form of a k-d tree.

According to one embodiment, a reduced mesh is created for each of the two arches.

According to one embodiment of the invention, the limit envelope of the displacements of an arch with respect to the opposite arch is determined by implementing the following steps:
  using the mesh of one of said arches, a volumetric structure is created adapted to encompass all of the positions of said arch with respect to the opposite arch during the mandibular kinetics,
  for each position of the arch and for each voxel of said structure, the distance between the centre of said voxel and each node of the mesh of the opposite arch is determined, it is determined whether each voxel is located inside or outside the mesh of the opposite arch and the voxels that are located inside said mesh are memorised, said voxels translating a contact between the arches, said contacts are accumulated for all of the positions, using said memorised voxels, a surface is constructed representing the limit envelope of the displacements of the teeth, on said surface, a map of the contacts and/or a map of the distances between the teeth of the two arches is displayed.

In a particularly advantageous manner, to record the mandibular kinetics, the patient is equipped with markers attached directly to the teeth of the mandibular arch or to the mandible through a support.

The invention also relates to the use of the method described above to design a dental prosthesis to implant on an arch of the patient, comprising:

obtaining a first mesh of said arch, using said first mesh, implementing the method to generate a mapping of the contacts and/or the distances between the teeth of the mandibular and maxillary arches, adjusting a model of the prosthesis so as to optimise the contacts and/or the distances obtained when the model of the prosthesis is integrated in said first mesh.

Next, the design of the prosthesis may comprise:

obtaining a second mesh of the arch presenting the teeth prepared to receive said prosthesis, applying the mandibular kinetics to the second mesh, designing the definitive prosthesis so as to respect the contacts and/or distances obtained with the adjustment made on the first mesh.

The invention also relates to a computer programme product comprising a set of instructions which, once loaded on a computer, enable the implementation of the method as described previously.

Said product may be on any computer support, such as for example a memory or a CD-ROM.

BRIEF DESCRIPTION OF THE DRAWINGS

Other characteristics and advantages of the invention will become clear from the detailed description that follows, with reference to the appended drawings, in which.

DETAILED DESCRIPTION OF THE INVENTION

Obtaining Meshes of the Maxillary Arch and the Mandibular Arch

Prior to the implementation of the method, the dental arches have been scanned in occlusion position with a known and reproducible relationship. A tool that can be used for this purpose is an intrabuccal optical imprint camera. One arch is scanned then the other, as well as a vestibular imprint (on the side) of the teeth in occlusion position to know the position of one arch with respect to the other. This operation is known per se and does not as such form part of the invention. Another method could consist in using a table scanner. This scans the plaster models derived from physical-chemical imprints one after the other then occlusion position. The invention may in fact be implemented with a 3D model of the dental arches generated by commercially available techniques.

The result of these scannings is a surface mesh of the maxillary arch and the mandibular arch. Each mesh is defined in an orthonormal coordinate system of the scanner.

Recording of the Mandibular Kinetics

The aim of recording the mandibular kinetics is to make it possible to know the manner in which the mandible is displaced in space, and to use said kinematics to animate three-dimensional models of the dental arches with a view to guiding the design of a dental prosthesis or of another correction device (orthodontic apparatus, mouth guard, etc.).

One embodiment of this recording, as well as the registration of the dental arches relative to reference planes or axes of the patient has already been described in document WO 2013/030511 and may be implemented in the present invention, the invention not however being limited to the techniques described in this document.

Generally speaking, the recording of the mandibular kinetics is implemented by equipping the patient with a marker attached to the forehead of the patient and markers attached directly to the teeth of the mandibular arch or to the mandible through a support, and by locating and recording the displacements of said markers by means of a camera during mandibular movements of the patient.

Figure 1:
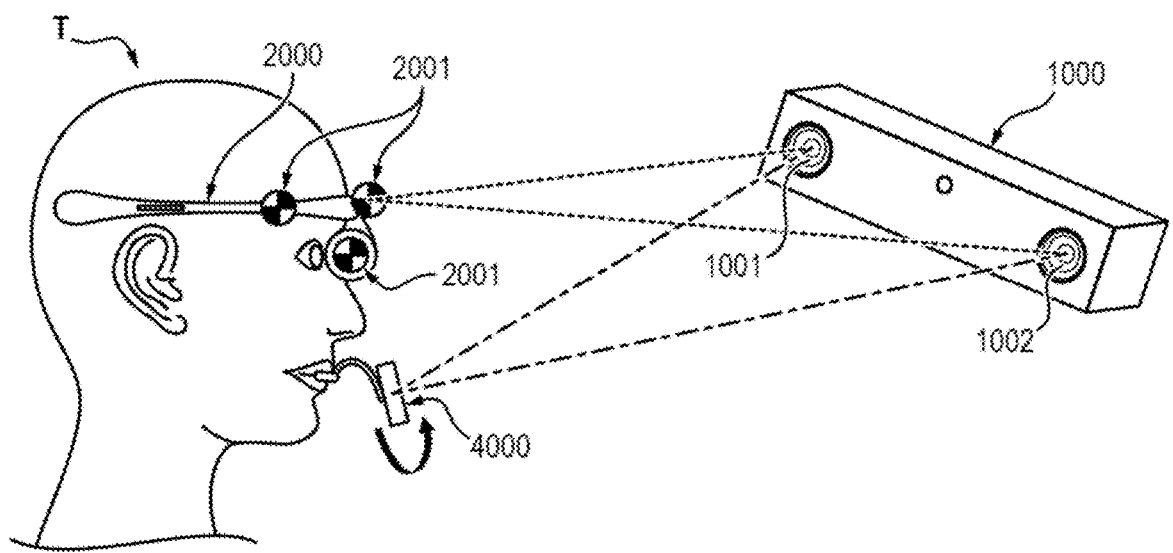
FIG. 1 is a schematic diagram illustrating the recording of the mandibular kinetics.

FIG. 1 is a schematic diagram illustrating the recording of the mandibular kinetics.

An arch 4000 attached to the teeth bearing markers detectable by a camera 1000 is put in place on the mandible of the patient. Alternatively, it is possible to use a mouth guard (not illustrated).

The patient is furthermore also equipped with a frontal headset 2000 bearing markers 2001 detectable by said camera 1000.

In the example illustrated, the camera 1000 is a stereoscopic camera comprising two lenses 1001, 1002.

It is however possible to use any other type of commercially available camera, subject to equipping the frontal headset and the arch attached to the mandible with markers detectable by said camera.

These markers may be diodes tracked by the camera. But they may be black and white targets or colours or spheres, chips or other reflective objects. The displacement of the markers of the mandible is tracked by the camera 1000 and does so with respect to the markers 2001 of the forehead. A rigid transformation makes it possible to deduce the movement of the 3D model of the mandibular arch compared to the 3D maxillary model.

The model of the maxillary arch and the reference planes are associated with the animation of the mandible in movement. In the software it is possible to display or to hide each of these elements.

Creation of a Simplified Mesh of an Arch

Since the computations require an important graphic resource, the three-dimensional models of the arches are re-dimensioned in order to enable the implementation of the method on most computers.

To this end, in the three-dimensional model of an arch, which is constituted of a surface mesh, only the cells in which the nodes (apices) are located at a distance of less than 1 cm from the opposite arch are conserved. The other cells will not be taken into account in the computation.

This reduced mesh is obtained at least for the arch on which it is wished to display the map of contacts and/or the map of distances. However, it is also possible to create this reduced mesh for the opposite arch, notably if it is wished to display the maps of contacts and/or distances on the models of the two arches.

Next, a pre-computation step is implemented in the background using the aforementioned reduced (or simplified) mesh. Certain values are invariant, such as the distance between the meshes of the two arches. An algorithm for computing the distance between a point and a three-dimensional cell (for example a triangle, although the form of the cells can be different) is applied and conserved in a memory in order to materialise later virtually the contact zones. Next, a bounding box is associated with each cell of the simplified mesh. Said box is composed of several volumetric elements, also called "voxels". For each voxel of the bounding box, the software detects whether there is contact or not, that is to say whether the nodes of the mesh of the opposite arch are likely to enter into confrontation with these voxels. This layout or network of contacts is designated by the term "contact grid".

K-d Tree

According to an advantageous embodiment, the network of contacts is partitioned spatially in the form of a k-d tree. This layout enables an optimised spatial subdivision of space, which makes it possible to speed up data processing.

Mapping of Contacts

The map of contacts is intended to inform the practitioner of the existence or not of a contact between the two arches, without distance information. The sensitivity may be adjusted as desired.

Typically, a contact sensitivity between −200 μm and +200 μm may be retained.

According to one embodiment, the map of contacts may be displayed in a static manner on the mesh of one of the arches. To this end, a colour representative of the existence of a contact is applied to each cell containing a node for which a contact has been detected, and said colour is displayed on each respective cell of the mesh of the arch.

According to another embodiment, the map of contacts may be displayed in a dynamic manner, that is to say that the mandibular kinetics is applied to animate the meshes of the arches and the display of colour during this animation is updated.

Advantageously, this display may be associated with a "shooting star" type effect enabling the trace of the contact on the arch concerned to be followed. To this end, the display of the contact zones for the previous position is temporarily conserved. This effect is obtained by computing the colour zone to display as a function of the age of the last contact. Potentially, the trace of the contact is progressively attenuated.

Figure 2:
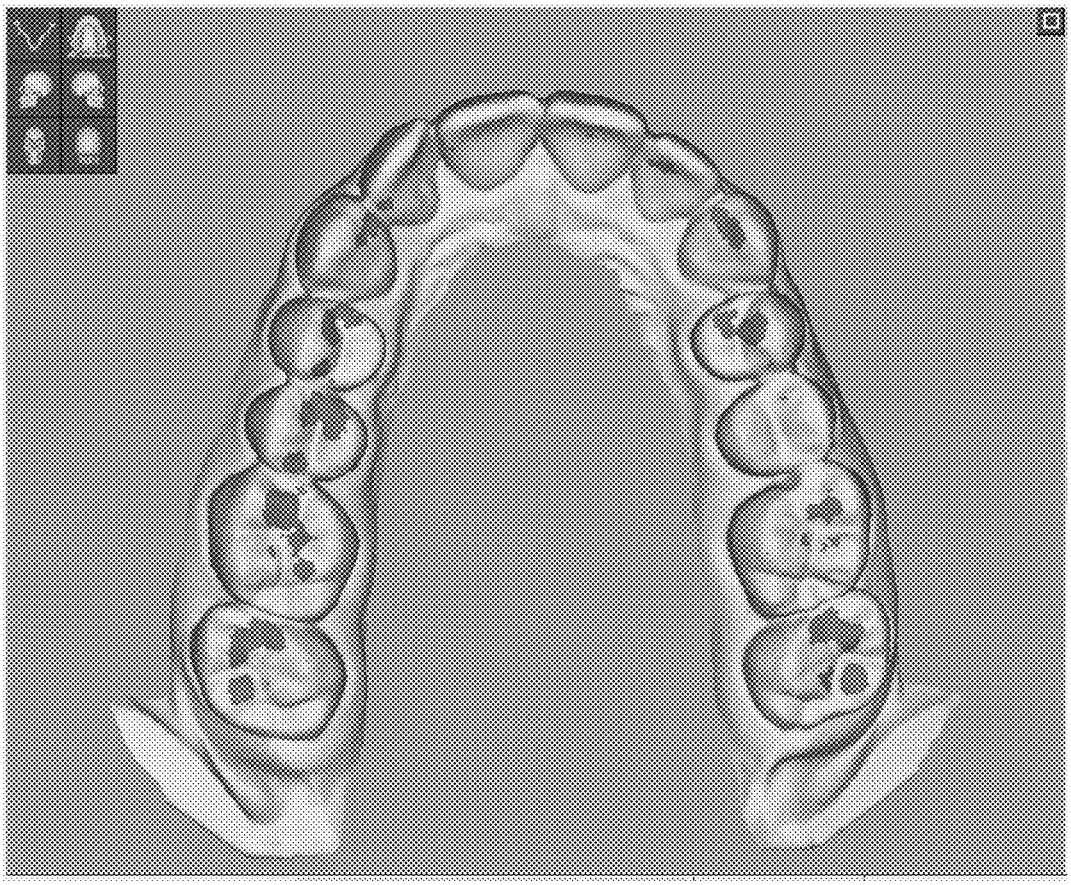
FIG. 2 illustrates a display screen of a map of contacts.

FIG. 2 illustrates an example of such a map of contacts displayed on the mesh of an arch.

Mapping of Distances

The map of distances is intended to supply to the practitioner information on the distance between the two arches by means of a colour code.

This colour code also makes it possible to signal the proximity of a contact. To this end, at the approach of a contact between the two meshes, the colour of the cells of the mesh concerned is different to the colour applied when the two meshes touch.

To construct the map of distances, the software processes all the nodes of the arch concerned in such a way as to determine, for each of said nodes, the nodes of the opposite arch that are the closest.

Advantageously, the aforementioned k-d tree is used for this purpose. Using the nodes thereby determined, it is possible to determine which cells touch the mesh of the opposite arch.

The colour code is next deduced for each node of the mesh, as a function of the distance calculated by the algorithm.

As for the aforementioned map of contacts, the map of distances may be displayed in a dynamic manner, that is to say that the mandibular kinetics is applied to animate the meshes of the arches and the display of colour during this animation is updated.

Figure 3:
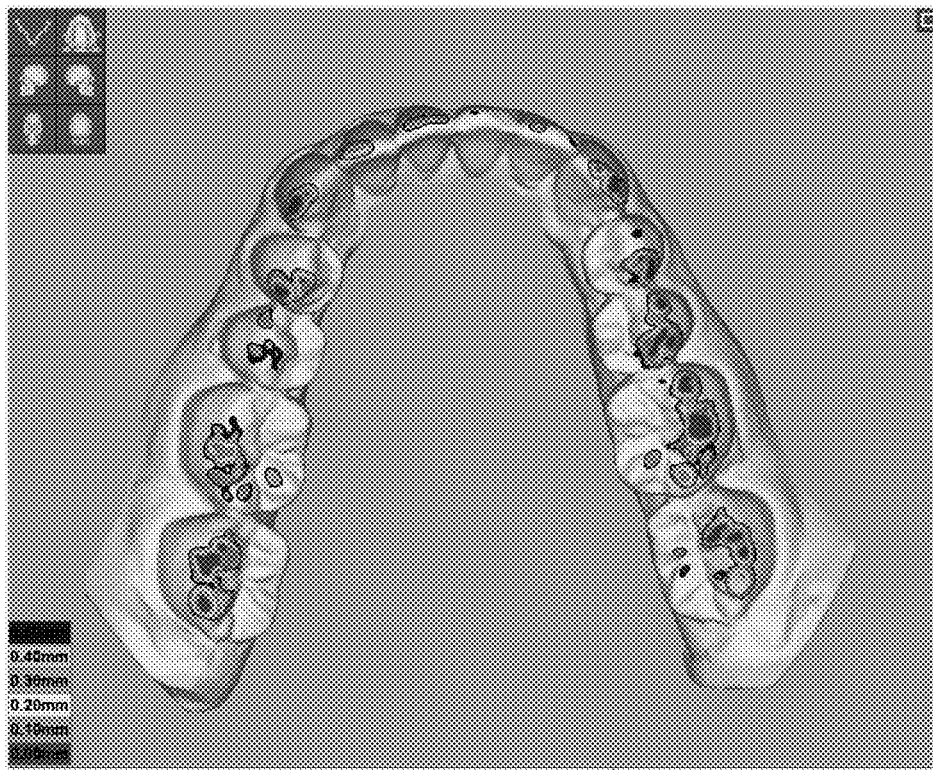
FIG. 3 illustrates a display screen of a map of distances.

FIG. 3 illustrates a polychrome map of distances indicating the proximity of the dental contacts.

Determination of the Limit Envelope of Displacements of an Arch with Respect to the Opposite Arch This envelope is also designated by the acronym FGP (Functionally Generated Path).

This surface materialises the limit envelope of dental displacements in space. This surface is notably used in the computer aided design of dental prostheses, in order to ensure that their shape is integrated in the movement of antagonistic teeth without clashing or discomfort.

This envelope may be calculated either for the mandibular arch, or for the maxillary arch, it being understood that only the mandibular arch is mobile. To calculate the maxillary FGP, it is considered that the mandible is immobile and the movement is transposed to the maxillary arch.

To determine the FGP, a volumetric structure comparable to a bounding box of the complete arch is adapted to the arch of which it is wished to obtain the FGP. The mark obtained during scanning of the opposite arch to that for which it is wished to obtain the FGP is advantageously chosen for orthonormal mark.

The volumetric structure must thus have a sufficient size to contain the different positions of the arch that are going to constitute the FGP. This structure is positioned in the mark of the scanner of the opposite arch.

Next, for each voxel of the volumetric structure, the distance is computed between the centre of said voxel and a cell of the mesh of the opposite arch. This computation makes it possible to determine whether there exists or not a contact, for all the positions of the arch and for each cell of the mesh of the opposite arch.

The normal to each cell of the mesh of the opposite arch makes it possible to determine whether the voxel is located inside or outside the mesh. The voxels located inside, that is to say the voxels translating a contact between the two arches, are then kept in a memory. A volumetric structure accumulating all the contacts, for all the positions, is thereby obtained.

Figure 4:
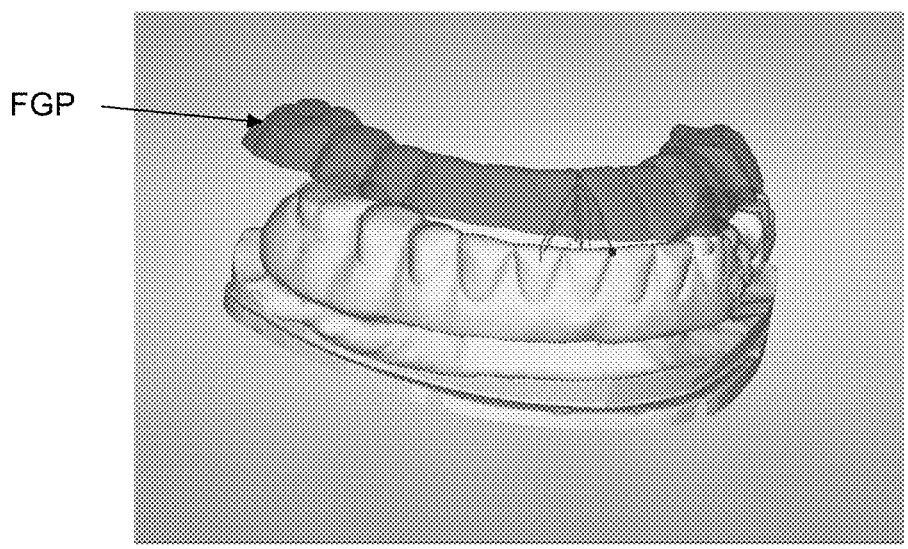
FIG. 4 illustrates an FGP and the model of the corresponding arch.

Applying the "marching cubes" algorithm makes it possible to construct, using the memorised voxels, the surface of the FGP. FIG. 4 illustrates the FGP thereby determined (transparent view) and the subjacent model the corresponding arch.

As for the meshes of the arches, it is possible to display a map of distances or a map of contacts with respect to the opposite arch on the surface of the FGP.

Figure 5:
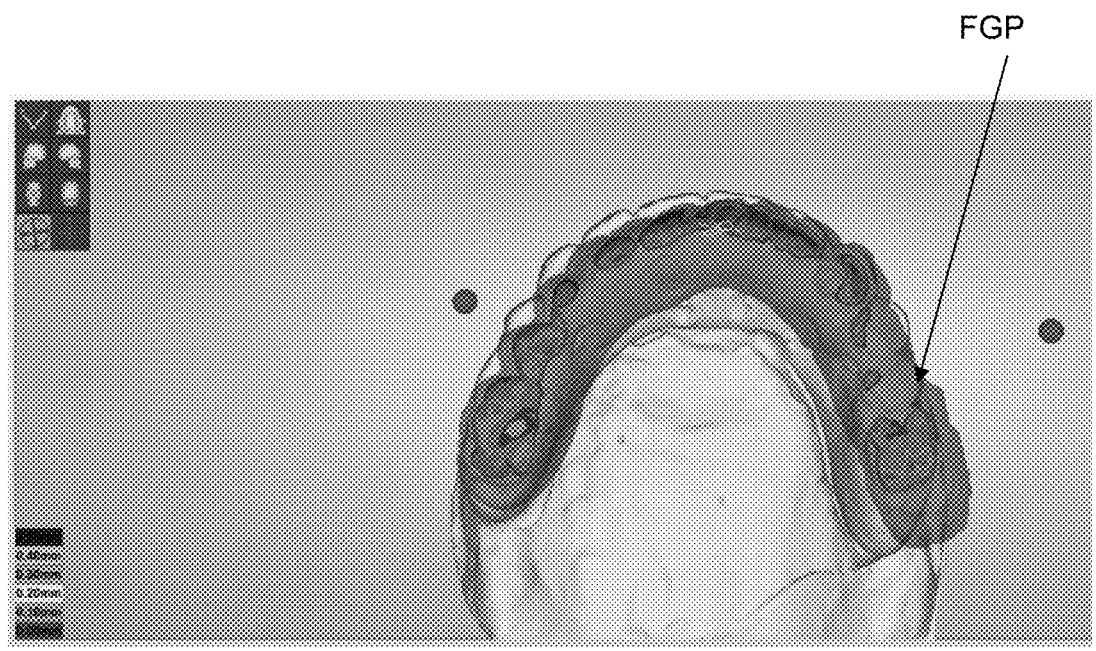
FIG. 5 illustrates a display screen of a map of distances on an FGP.

FIG. 5 thus illustrates a display of the map of distances between the FGP and the mesh of the maxillary arch.

Design of a Dental Prosthesis

To design a dental prosthesis, it is possible to validate the contacts between models of arches bearing teeth restored with provisional prostheses (or instead models of arches bearing unprepared teeth), then replacing these first models by second models comprising teeth prepared to receive the definitive prostheses. This validation may potentially comprise successive adjustment steps.

Indeed, it is possible to correlate, in so far as there are sufficient points of association between two meshes, the first and second 3D models of the arches between them. One of the methods used is to click and position reference points on the two meshes at the level of recognisable zones. An automatic recognition may refine the correlation.

Once the new model associated, the mandibular kinetics recorded for the first model is associated with the second to animate it in the same manner.

The interest is to control and validate the displacements as well as to carry out prosthetic restorations that are integrated in the mastication movements of the patient when the practitioner estimates at the provisional prosthesis step that the kinematics are correct and functional. The second model may be a model integrating the teeth prepared ready to receive definitive prostheses of all types.

Export of Data

All of the data obtained during the implementation of the method may be memorised and exported to computer aided design software. These data may include the position of the arches with respect to each other, the reference planes, the occlusal cap, the anatomic points, the bicondylar axis and the FGP.

The design of dental prostheses, orthotic devices or occlusal mouth guards takes into account these data to guide the design.

What is more, the elements supplied by the software can be produced by means of a 3D printer. The position of the models with respect to each other may be maintained thanks to an occluder. Interchangeable models of the FGP may be mounted on this same occluder, which allows the prosthetist to modify the design manually to adjust the occlusion. The prosthetist thus has at his disposal information on the manner in which the opposite arch to the working model is displaced in space, without using an articulator.

REFERENCES

WO 2013/030511

The invention claimed is:

1. A method for determining a mapping of contacts and/or distances between teeth of a maxillary arch and a mandibular arch of a patient, comprising the following steps:
   obtaining mandibular kinetics recorded on the patient, said mandibular kinetics being recorded by locating and by recording, by means of a camera, displacements of markers attached on the one hand to the forehead of the patient and on the other hand to the mandibular arch, during mandibular movements of the patient,
   obtaining surface meshes of the maxillary arch and the mandibular arch and registering said surface meshes relative to one another,
   creating a reduced mesh of at least one of said arches, comprising selecting, in a surface mesh of the at least one of said arches, cells in which nodes are located at a distance of less than 1 cm from a surface mesh of an opposite arch,
   creating, for each cell of said reduced mesh of the at least one of said arches, a bounding box comprising a plurality of voxels surrounding said cell,
   using the mandibular kinetics, calculating a network of contacts comprising, for each voxel of the bounding box, information on the existence of a contact between said voxel and a node of the surface mesh of the opposite arch during a relative movement of the mandibular arch in relation to the maxillary arch,
   for each node of said reduced mesh, determining, using the network of contacts, the existence or not of a contact between said node and a node of the surface mesh of the opposite arch,
   applying a colour representative of the existence of a contact to each cell comprising a node for which a contact has been detected, and
   displaying said colour on each respective cell of the surface mesh of the at least one of said arches, so as to form a map of the contacts between the teeth of the maxillary arch and the mandibular arch,
   wherein the mandibular kinetics is applied to animate the surface meshes of the maxillary arch and the mandibular arch and the display of colour is updated during this animation.

2. The method according to claim 1, wherein during the updating of the display, a previous display is temporarily conserved and it is progressively attenuated.

3. The method according to claim 1, wherein the reduced mesh is partitioned in the form of a k-d tree.

4. The method according to claim 1, wherein a reduced mesh is created for each of the maxillary arch and the mandibular arch.

5. The method according to claim 1, wherein, to record the mandibular kinetics, the patient is equipped with markers attached directly to the teeth of the mandibular arch or to the mandible through a support.

6. A method for determining a mapping of contacts and/or distances between teeth of a maxillary arch and a mandibular arch of a patient, comprising the following steps:
   obtaining mandibular kinetics recorded on the patient, said mandibular kinetics being recorded by locating and by recording, by means of a camera, displacements of markers attached on the one hand to the forehead of the patient and on the other hand to the mandibular arch, during mandibular movements of the patient,
   obtaining surface meshes of the maxillary arch and the mandibular arch and registering said surface meshes relative to one another,
   creating a reduced mesh of at least one of said arches, comprising selecting, in a surface mesh of the at least one of said arches, cells in which nodes are located at a distance of less than 1 cm from a surface mesh of an opposite arch,
   creating, for each cell of said reduced mesh of the at least one of said arches, a bounding box comprising a plurality of voxels surrounding said cell,
   using the mandibular kinetics, calculating a network of contacts comprising, for each voxel of the bounding box, information on the existence of a contact between said voxel and a node of the surface mesh of the opposite arch during a relative movement of the mandibular arch in relation to the maxillary arch,
   for each node of the reduced mesh, determining, using the network of contacts, the distance between said node and a node of the surface mesh of the opposite arch,
   applying a colour representative of said distance to each cell comprising said node, and
   displaying said colour on each respective cell of the surface mesh of the arch, so as to form a map of the distances between the teeth of the maxillary arch and the mandibular arch, wherein the mandibular kinetics is applied to animate the surface meshes of the maxillary arch and the mandibular arch and the display of colour is updated during this animation.

7. A method for determining a mapping of contacts and/or distances between teeth of a maxillary arch and a mandibular arch of a patient, comprising the following steps:

obtaining mandibular kinetics recorded on the patient, said mandibular kinetics being recorded by locating and by recording, by means of a camera, displacements of markers attached on the one hand to the forehead of the patient and on the other hand to the mandibular arch, during mandibular movements of the patient, obtaining surface meshes of the maxillary arch and the mandibular arch and registering said surface meshes relative to one another, creating a reduced mesh of at least one of said arches, comprising selecting, in a surface mesh of the at least one of said arches, cells in which nodes are located at a distance of less than 1 cm from a surface mesh of an opposite arch, creating, for each cell of said reduced mesh of the at least one of said arches, a bounding box comprising a plurality of voxels surrounding said cell, using the mandibular kinetics, calculating a network of contacts comprising, for each voxel of the bounding box, information on the existence of a contact between said voxel and a node of the surface mesh of the opposite arch during a relative movement of the mandibular arch in relation to the maxillary arch, using the surface mesh of one of said arches, a volumetric structure is created adapted to encompass all of the positions of the at least one of the arches with respect to the opposite arch during the mandibular kinetics, for each position of the at least one of the arches and for each voxel of said structure, the distance is determined between the centre of said voxel and each node of the surface mesh of the opposite arch, it is determined whether each voxel is located inside or outside the surface mesh of the opposite arch and the voxels that are located inside said surface mesh are memorised, said voxels defining a contact between the maxillary arch and the mandibular arch, said contacts are accumulated for all of the positions, using said memorised voxels, a surface is constructed representing the limit envelope of the displacements of the teeth, on said surface, a map of the contacts and/or a map of the distances between the teeth of the maxillary arch and the mandibular arch is displayed.

8. A method of designing a dental prosthesis to implant on an arch of a patient, the method comprising:

obtaining a first mesh of said arch, using said first mesh, implementing the method of claim 1 to generate a mapping of the contacts and/or distances between the teeth of the mandibular and maxillary arches, adjusting a model of the dental prosthesis so as to optimise the contacts and/or distances obtained when the model of the dental prosthesis is integrated in said first mesh.

9. The method of claim 8, further comprising:

obtaining a second mesh of the arch presenting the teeth prepared to receive the dental prosthesis, replacing the first mesh by the second mesh, applying the mandibular kinetics to the second mesh, designing a definitive prosthesis so as to respect the contacts and/or distances obtained with the adjustment made on the first mesh.

10. A non-transitory computer-readable medium encoded with a computer program comprising a set of instructions which, once loaded on a computer, enable the implementation of the method according to claim 1.

* * * * *